United States Patent [19]  
Mohrbacher et al.

[11] Patent Number: 4,888,335  
[45] Date of Patent: Dec. 19, 1989

[54] 3-ALKOXY-2-AMINOPROPYL HETEROCYCLIC AMINES AND THEIR USE AS CARDIOVASCULAR AGENTS

[75] Inventors: Richard J. Mohrbacher, Maple Glen; Philip P. Grous, Philadelphia, both of Pa.

[73] Assignee: McNeilab, Inc., Spring House, Pa.

[21] Appl. No.: 223,985

[22] Filed: Jul. 25, 1988

[51] Int. Cl.$^4$ .................. C07D 403/06; C07D 413/06
[52] U.S. Cl. ..................... 514/217; 540/479; 540/550; 540/591; 540/597; 540/598; 540/602; 544/42; 544/102; 546/104
[58] Field of Search ............... 540/591; 549/597, 598, 549/602; 514/217

[56] References Cited

U.S. PATENT DOCUMENTS

| Re. 30,577 | 4/1981 | Busch et al. | 260/326.5 |
| 4,555,514 | 11/1985 | Combourieu et al. | 514/343 |
| 4,727,072 | 2/1988 | Grous et al. | 514/230 |
| 4,758,563 | 7/1988 | Grous et al. | 514/223.8 |

FOREIGN PATENT DOCUMENTS

| 85/37537 | 7/1985 | Australia . |
| 138684 | 4/1985 | European Pat. Off. . |
| 146155 | 6/1985 | European Pat. Off. . |
| 146159 | 6/1985 | European Pat. Off. . |
| 237191 | 9/1987 | European Pat. Off. . |
| 2558159 | 7/1985 | France . |
| WO83/02274 | 7/1983 | PCT Int'l Appl. . |

Primary Examiner—David B. Springer

[57] ABSTRACT

Propylamines of the formula (I):

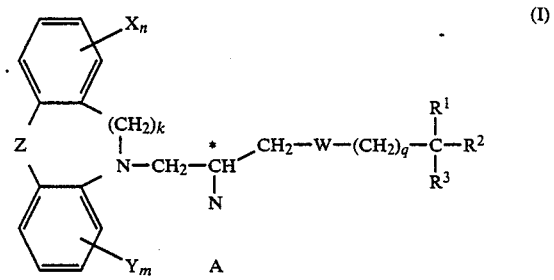

and isomers thereof, particularly those enantiomers and racemates relative to the chiral carbon indicated by an asterisk (*). The propylamines can be used for the treatment of hypertension or angina in humans. A is pyrrolidine, piperidine or morpholine, Z is alkylene, alkenylene, oxygen or a sulfur atom and W is an oxygen or a sulfur atom.

20 Claims, No Drawings

3-ALKOXY-2-AMINOPROPYL HETEROCYCLIC AMINES AND THEIR USE AS CARDIOVASCULAR AGENTS

Various ethers are known to be effective cardiovascular pharmaceuticals as described in U.S. Pat. No. 4,555,514; U.S. Pat. No. Re. 30,577; PCT Publication No. 83/02274; Australian Pat. No. 85/37537; French Brevet No. 2,558,159; and European Patent Application Nos. 138,684; 146,155; 146,159 and 237,191.

SUMMARY OF THE INVENTION

Propylamines of the following formula (I):

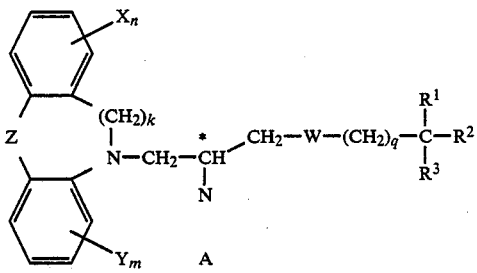

are provided as antihypertensive and anti-anginal agents which can be used in a manner similar to bepridil. In formula (I), $R^1$-$R^3$ are hydrogen, alkyl, alkenyl, or —$CR^1R^2R^3$ represents a lower alkenyl group or $R^1$-$R^3$ are joined to form cycloalkyl, A is pyrrolidine, piperidine or morpholine, W is oxygen or sulfur, X, Y and Z are as described, k and q are the integers 0 or 1, and m and n are the integers 0, 1, 2 or 3.

DETAILED DESCRIPTION OF THE INVENTION

In more detail, the invention includes propylamines of the following formula (I):

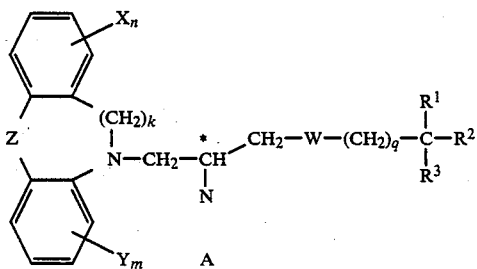

wherein $R^1$, $R^2$ and $R^3$ are independently hydrogen, lower alkyl or lower alkenyl groups or —$CR^1R^2R^3$ represents a lower alkenyl group, or $R^1$ is a hydrogen, lower alkyl or lower alkenyl group and $R^2$ and $R^3$ are joined to form a cycloalkyl group of about 3 to 8 carbons or $R^1$, $R^2$ and $R^3$ are joined to form a polycyclicalkyl group of about 7 to 12 carbons;

W is an oxygen or a sulfur atom;

X is independently selected from the group consisting of halo, lower alkyl, lower alkoxy, trifluoromethyl, hydroxy, or, when n is 2 on adjacent carbons, methylenedioxyl;

Y is independently selected from the group consisting of halo, lower alkyl, lower alkoxy, trifluoromethyl, hydroxy, or, when m is 2 on adjacent carbons, methylenedioxyl;

Z is —$(CH_2)_p$—, —$CR^4$=$CR^5$—, —$CHR^4$—$CHR^5$— or an oxygen or a sulfur atom;

$R^4$ is hydrogen or lower alkyl;

$R^5$ is hydrogen or lower alkyl;

A represents the atoms necessary to form a pyrrolidine, piperidine or morpholine ring;

k is 0 or 1;

m is 0, 1, 2 or 3;

n is 0, 1, 2 or 3;

p is 1, 2 or 3;

q is 0 or 1, and the pharmaceutically acceptable acid addition salts thereof.

Within the scope of $R^1$, $R^2$ and $R^3$ are hydrogen; lower alkyl of about 1 to 8 carbons such as methyl, ethyl, n-propyl and iso-propyl; lower alkenyl groups of about 2 to 8 carbons such as allyl, propenyl and 1-butenyl, or —$CR_1R_2R_3$ represents lower alkenyl, e.g. of 2 to 5 carbons such as an allyl group, the individual $R^1$, $R^2$ and $R^3$ groups being independently chosen, with methyl being particularly preferred. Particular definitions of $R^1$-$R^3$ are those where $R^1$ is hydrogen and $R^2$ and $R^3$ are both methyl or where $R^1$, $R^2$ and $R^3$ are each methyl. A second particular definition of $R^1$-$R^3$ is where $R^1$ is hydrogen, lower alkyl or lower alkenyl as described above, e.g. methyl, and $R^2$ and $R^3$ are joined together to form a saturated carbocyclic moiety of about 3 to 8 carbons, e.g. a cyclopenyl or cyclohexyl ring. A third particular arrangement for $R^1$—$R^3$ is where all three are joined to form a polycyclicalkyl group of about 7 to 12 carbons e.g. 1-adamantyl, 1-bicyclo[2.2.2]octane or 1-bicyclo[2.2.1]heptane.

Within the scope of $R^4$ and $R^5$ are hydrogen and alkyl of about 1 to 4 carbons such as methyl, ethyl, n-propyl and iso-propyl. In particular, $R^4$ and $R^5$ are both hydrogen.

Within the scope of Z is —$(CH_2)_p$— where p is the integer 1, 2 or 3, particularly 1; —$CR^4$=$CR^5$—, particularly where $R^4$ and $R^5$ are both hydrogen; or an oxygen or a sulfur atom. A represents particularly the atoms necessary to form a pyrrolidine ring, and q is 0 or 1, particularly 1.

X is independently selected from the group consisting of halo such as fluoro, chloro, bromo or iodo; loweralkyl of about 1 to 6 carbons such as methyl, ethyl, or n-hexyl; lower alkoxy of about 1 to 6 carbons such as methoxy, ethoxy or n-hexoxy; trifluoromethyl; hydroxy; or, when n is 2 on adjacent carbons, methylenedioxy. Preferably, n is 0.

Y is independently selected from the group consisting of halo such as fluoro, chloro, bromo or iodo; loweralkyl of about 1 to 6 carbons such as methyl, ethyl, or n-hexyl; lower alkoxy of about 1 to 6 carbons such as methoxy, ethoxy or n-hexoxy; trifluoromethyl; hydroxy; or, when m is 2 on adjacent carbons, methylenedioxy. Preferably, m is 0.

Particular examples of compounds of the invention of formula (I) are:

(1) 5,6-dihydro-5-[3-(2-methylpropoxy)-2-(1-pyrrolidinyl)propyl]-11H-dibenz [b,e]azepine;

(2) 5,6,11,12-tetrahydro-5-[3-(2-methylpropoxy)-2-(1-pyrrolidinyl)propyl]dibenz[b,f]azocine;

(3) 5,6-dihydro-5-[3-(2,2-dimethylpropoxy)-2-(1-pyrrolidinyl)propyl]-11H-dibenz[b,e]azepine;

(4) 10,11-dihydro-5-[3-(2-methylpropoxy)-2-(1-pyrrolidinyl)propyl]-5H-dibenz[b,f]azepine;

(5) 10,11-dihydro-10-[3-(2,2-dimethylpropoxy)-2-(1-pyrrolidinyl)propyl]dibenz[b,f][1,4]oxazepine;
(6) 5-[3-(2,2-dimethylpropoxy)-2-(1-pyrrolidinyl)]-propyl]5H-dibenz[b,f]azepine;
(7) 10-[3-[(1-methylcyclohexyl)methoxy]-2-(1-pyrrolidinyl)propyl]10H-phenoxazine;
(8) 5-[3-[(1-methylcyclohexyl)methoxy]-2-(1-pyrrolidinyl)propyl]-5H-dibenz[b,f]azepine;
(9) 10-[3-(2-methylpropoxy)-2-(1-pyrrolidinyl)propyl]-10H-phenothiazine; and
(10) 5-[3-(2-methyl-2-propenoxy)-2-(1-pyrrolidinyl)-propyl]-5H-dibenz[b,f]azepine.

Representative salts of the compounds of formula (I) which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, 2-acetoxybenzoic or a salt made with saccharin. Such salts can be made by reacting the free base of a compound of formula (I) with the acid and recovering the salt.

Compounds of formula (I) and other compounds of the invention may exist in various isomeric forms, e.g. in view of the presence of an asymmetric carbon atom or a carbon-carbon double bond. It is understood that the present invention includes all such individual isomers, their racemates and cis- and trans isomers. Particular isomers include those enantiomers and racemates relative to the chiral carbon indicated by an asterisk (*) in the formula (I) compounds. Such individual isomers may be obtained by methods known in the art, e.g. by initiating the synthesis with optically active starting materials or reagents or by separation of racemic intermediates or final products, e.g. as described in "Stereochemistry of Carbon Compounds", by Ernest L. Eliel, McGraw-Hill, New York (1962). Also within the scope of the invention are compounds of the invention in the form of hydrates and other solvate forms. As used herein, the term "alkyl" and "alkoxy" denotes straight or branched chain alkyl grouping.

To prepare the compounds of the present invention having formula (I), one may use the reaction sequence summarized in the following Reaction Scheme wherein R is used to refer to the $-(CH_2)_q-C(R^1R^2R^3)$ moiety in formula (I) and the remaining symbols are as defined for the formula (I) compounds, e.g. the A ring X, Y, etc.

Reaction Scheme:

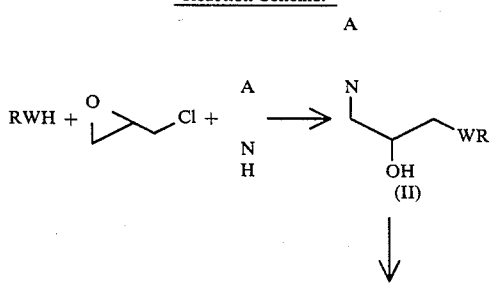

-continued
Reaction Scheme:

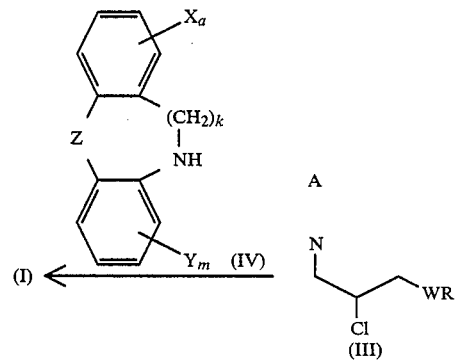

Alcohols of formula RWH wherein W is oxygen may be obtained commercially, prepared as known in the art or synthesized from the corresponding acid of formula $(R^1R^2R^3C)COOH$ by reduction, e.g. with borane or other reducing agents. Thiols of the formula RWH wherein W is a sulfur atom may be obtained commercially or prepared by methods known in the art or analogous methods thereto. Epichlorohydrin and the A=NH ring heterocyclic compounds are commercially available or known in the literature or may be synthesized by analogous methods to those described in the literature.

Amino alcohols of the formula (II) may be prepared by stirring 1.0 mole of the starting alcohol RWH and 1.0 mole of epichlorohydrin and adding 0.001 mole of a Lewis Acid such as titanium (IV) chloride, zinc (II) chloride, boron trifluoride or tin (IV) chloride. The reaction temperature rises to about 130° C. in a few seconds and the mixture is stirred until the reaction temperature is about 40° C. followed by the addition of 1.0 mole of the A=NH ring heterocycle. The reaction mixture is stirred and heated on a steam bath for about 1 hour, allowed to cool to RT and sodium or potassium hydroxide solution containing 1 mole of hydroxide is added with stirring. The reaction mixture is heated on a steam bath for about 30 minutes, then cooled to RT, partitioned between cold water and ether and the ether layer is separated and dried. The solvent is removed and the residue distilled under reduced pressure to give the amino alcohol (II).

The intermediate (II) is then reacted with a chlorinating agent such as $PCl_5$, $PCl_3$ or $SOCl_2$ to yield the corresponding chloro compound of formula (III). In a typical procedure, 1.05 equivalents of $PCl_5$ in dry toluene is cooled to 10° C. and a mixture of 1.0 equivalents of an amino alcohol of formula (II) in dry toluene and excess hydrogen chloride is added dropwise while maintaining the temperature between 10°–5° C. After the addition is complete, the mixture is allowed to stir at RT for about 1.5 hr. The reaction mixture is then poured portionwise into excess cold potassium hydroxide solution while keeping the temperature between 25°–35° C. Stirring is continued for one-half hr after the addition and the mixture diluted with water and extracted with toluene or ether. The organic extract is washed with water and brine, dried and concentrated in vacuo at a temperature not exceeding 50° C. to yield the crude chloroamine of formula (III). The crude product is stored under argon until used.

Tricyclic amines of formula (IV) may be obtained commercially or prepared by methods known in the art or analogous methods thereto. Cyclic amine compounds of formula (IV) wherein k is 1 may be obtained by reduction of the corresponding lactam by the action of hydride reducing agents such as lithium aluminum hydride, for example, as described in L. H. Werner et al. in J. Med. Chem., Vol. 8, pp 74–80 (1965). Amines of formula (IV) wherein Z is an alkene moiety of the type —CH=CH— may be prepared by standard methods of reduction of a precursor ketone to the corresponding alcohol and dehydration of the alcohol to form the alkene moiety. Compounds of formula (IV) wherein one of $R^4$ or $R^5$ is alkyl may be obtained by treatment of a precursor ketone with a Grignard reagent of the formula $R^4MgBr$ or $R^5MgBr$ to produce an intermediate alcohol and subsequent dehydration of the alcohol to produce an $R^4$ or $R^5$ alkene moiety of the type —$CR^4$=CH— or —CH=$CR^5$—. Compounds of formula (IV) wherein both $R^4$ and $R^5$ are alkyl may be prepared from the appropriate $\alpha$—$R^4$ or —$R^5$ substituted ketone and then following the Grignard/dehydration technique to produce formula (IV) compounds where Z is —$CR^4$=$CR^5$—.

The chloro compound of formula (III) may then be reacted directly with the amine of formula (IV) to produce compounds of formula (I). Reaction of the chloro compound (III) to produce (I) involves a transition state moiety formed by loss of Cl⁻ and migration of the N—A ring to the carbon which formerly carried the chlorine In more detail, an amine of formula (IV) is stirred with about 1.0 to 1.2 equivalents of a strong base such as sodium hydride or a mixture of sodium hydride and 1 to 10% potassium hydride in an aprotic solvent such as toluene at a temperature of about 100° C. under an atmosphere of argon or nitrogen. After about 1 hr, the mixture is treated dropwise with a solution of about 1.0 to 1.3 equivalents of a chloro compound of formula (III) in an aprotic solvent such as toluene. The reaction mixture is then heated to reflux and stirred for a period of about 4 to 80 hr, cooled to RT and partitioned between water and toluene and/or ether. The organic portion is purified by chromatography, distillation and/or crystallization of the free base or an acid addition salt thereof.

In an alternate procedure, a solution of 1.0 or more equivalents of methyl lithium in ether is added drop wise to a stirred solution of 1.0 equivalents of an amine of formula (IV) in dry THF under argon or dry nitrogen. The reaction mixture is stirred for 1 or more hours, a solution of 1.0 equivalents of (III) in dry THF is added dropwise and the reaction mixture is heated to reflux for 3 to 16 hr. The reaction mixture is cooled to room temperature, diluted with ether, extracted with water and the organic portion purified by chromatography, distillation or crystallization. Other alkyl lithium compounds that may be used in this alternate procedure are n-butyl lithium in hexane and sec-butyl lithium in cyclohexane.

The activity of compounds of formula (I) for the treatment of hypertension was determined using the Spontaneously Hypertensive Rat (SHR) test as described below.

Spontaneously Hypertensive Rat Test

In this test, the arterial pressure of adult spontaneously hypertensive rats (Charles River) is monitored directly via an aortic cannula. The SH rats are anesthetized with an inhalation anesthetic (ether). The left carotoid artery is isolated and cannulated. The tip of the cannula is advanced to the aorta and the cannula is exteriorized behind the neck at the level of the scapula. Animals are placed in individual cages, allowed to recover from the anesthetic and are kept unrestrained. The arterial cannula is connected to a pressure transducer which is attached to a recorder. The test compounds are administered to at least 3 rats at doses selected in the range of 0.1 to 100 mg/kg of body weight by i.p. or p.o. routes of administration. The arterial pressure and heart rate are monitored for a minimum of 24 hr. A test compound is considered to be active as an antihypertensive agent if the mean arterial pressure (MAP) indicates a fall ($\delta$MAP) of >15 mm of Hg. Each animal serves as its own control.

Langendorff Isolated Heart

In addition to their utility in the treatment of hypertension, the compounds of formula (I) are useful in the treatment of the symptoms of angina pectoris by virtue of their ability to dilate coronary arteries. Their activity was measured using the "Langendorff's isolated heart" preparation. This test has been described in "Pharmacological Experiments on Isolated Preparations", Staff of the Department of Pharmacology, University of Edinbourgh, 2nd Ed., Churchill Livingstone, N.Y., 1970, pp 112–119. The test compounds were administered at concentrations of 30.0, 10.0, 3.0, 1.0, 0.3, 0.1, 0.03 and 0.01 micromolar ($10^{-6}$ molar). The minimum concentration $EC_{30}$) needed to elicit a 30% increase in coronary flow is shown in Table I for compounds of formula (I).

In the treatment of hypertension, an anti-hypertensively effective amount of a compound of formula (I) may be used, e.g. about 0.5 to 250 mg for an average human in an oral dose. For angina, an anti-anginally effective amount may be about 1 to 250 mg for an average human in an oral dose. The doses can be given about 1–4 times per day depending on the particular agent and the severity of the condition.

The utility of compounds of formula (I) of the invention is demonstrated by results obtained in the above tests as shown in the following Table I.

TABLE I

| Cpd. of Example | Langendorff $EC_{30}(10^{-6}M)$ | SHR Dose | SHR Route | SHR $\delta$MAP |
|---|---|---|---|---|
| 1 | .013 | 30 | i.p. | −65 |
|  |  | 10 | i.p. | −37 |
| 2b | .150 | 30 | p.o. | −25 |
| 3c | .004 | 30 | p.o. | −2 |
|  |  | 10 | i.p. | −54 |
| 4 | .011 | 10 | i.p. | −65 |
| 5b | .04 | 10 | i.p. | −70 |
|  |  | 30 | p.o. | −20 |
| 6 | .001 | 10 | i.p. | −27 |
| 7d | .012 | 30 | p.o. | −24 |
| 8 | .0037 | 30 | p.o. | −12 |
| 9 | .30 | 30 | p.o. | −19 |
|  |  | 10 | i.p. | −22 |
| 10 | — | 30 | p.o. | −25 |

To prepare the pharmaceutical compositions of this invention, one or more compounds or salts thereof of the invention as the active ingredient, is intimately admixed with a pharmaceutical carrier according to conventional pharmaceutical compounding techniques, which carrier may take a wide variety of forms depending on the form of the preparation desired for administration, e.g. oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain per dosage until, e.g. tablet, capsule, powder, injection, teaspoonful and the like, from about 0.5 mg to about 500 mg of the active ingredient, and, preferably from about 1 mg to about 100 mg.

In the following examples and throughout the specification, the following abbreviations may be used: mg (milligrams); g (grams); kg (kilograms); ml (milliliters); m (moles); mm (millimoles); M (molar); N (normal); psi (pounds per square inch); mm (millimeters); mp (melting point); bp (boiling point); meq (milliequivalents); eq (equivalents); E (trans); Z (cis); LAH (lithium aluminum hydride); THF (tetrahydrofuran); DMF (N,N-dimethylformamide); HPLC (high pressure liquid chromatography); g.c. (gas chromatography); hr (hours); min (minutes); RT (room temperature); i.p. (intraperitoneal); p.o. (Per os, orally); and C, H, N, O, etc. (the chemical symbols for the elements). Unless otherwise indicated, all temperatures are reported in °C (degrees centigrade), all pressures in mm of Hg and all references to ether are to diethyl ether.

EXAMPLE 1

5,6-Dihydro-5-[3-(2-methylpropoxy)-2-(1-pyrrolidinyl)-propyl]-11H -dibenz[b,e]azepine (Formula (I): $R^1=H$; $R^2$, $R^3=CH_3$; W=oxygen; z=—$CH_2$—; A=pyrrolidine; k=1; m=0; n=0; q=1)

In a 500 ml three neck flask (argon atmosphere) was placed 100 ml of dry toluene, 9.76 g (0.05 mole) of morphanthridine [prepared by the method described by L. H. Werner et al. in J. Med. Chem, Vol. 8, pp 74–80 (1965)] and 2.64 g (0.055 mole) of 50% sodium hydride/mineral oil and a small scoop of potassium hydride/mineral oil. The reaction mixture was stirred and heated to 100° C. for one hour then a solution of 13.18 g (0.06 mole) of 1-[2-chloro-3-(2-methylpropoxy)propyl]pyrrolidine [Prepared by the method described in U.S. Pat. No. Re. 30,577, column 3, line 32 for the compound designated "1-(3-isobutoxy-2-chloro)propyl pyrrolidine", distilled at 99°–100 ° C./90 mm] in 15 ml of dry toluene was added dropwise to the hot reaction mixture. The reaction mixture was stirred and heated to reflux for 44 hr (added 10 ml of dry DMF at 20 hr point). The reaction mixture was cooled to RT and washed with water and with saturated brine. The organic layer was dried over anhydrous magnesium sulfate and concentrated to dryness in vacuo to give 21.99 g of crude oily product. The oil was purified by preparation HPLC (Waters Prep 500; silica column, acetone/hexane eluant, 1:6) to give 10.46 g of oil that crystallized on standing. The pure title compound was obtained by recrystallization from 2-propanol/water to yield 6.79 g of a light yellow solid, mp 47.5°–51.5° C.

Elemental Analysis Calculated for $C_{25}H_{34}N_2O$: C, 79.34; H, 9.03; N, 7.40. Found: C, 79.20; H, 9.04; N, 7.36.

EXAMPLE 2

5,6,11,12-Tetrahydro-5-beta-[3-(2-methylpropoxy)-2-(1-pyrrolidinyl) propyl]dibenz[b,f]azocine Hydrate (5:1)

(Formula (I): $R^1=H$; $R^2=CH_3$; $R^3=CH_3$; W=oxygen; z=—$(CH_2)_2$—; A=pyrrolidine; k=1; m=0; n=0; q=1)

(a) 5H -5,6,11,12 -Tetrahydro dibenz[b,f]azocine

In a two liter three neck round bottom flask (argon atmosphere) was placed 300 ml of dry THF and 30.06 g (0.8 mole) of LAH was added cautiously. The reaction mixture was stirred and a suspension of 89.31 g (0.4 mole) of 11,12-dihydrodibenz[b,f]azocin-6(5H)-one (Aldrich) in 400 ml of hot THF was added dropwise. After the addition, the reaction mixture was stirred and heated to reflux for 8.5 hr. The reaction mixture was cooled to RT and 60 ml of 1N sodium hydroxide was added with caution (hydrogen evolution). The reaction mixture was stirred and heated to reflux for 0.5 hr to give a white suspension. The solid was removed by filtration and washed with several portions of warm THF. The filtrate was concentrated to dryness in vacuo to give 82.5 g of white solid title compound of 99.5% purity by g.c. The product was used in the next step without further purification.

(b) 5,6,11,12-Tetrahydro-5-beta-[3-(2-methylpropoxy)-2-(1-pyrrolidinyl)propyl]dibenz[b,f]azocine Hydrate (5:1)

A mixture of 20.93 g (0.10 mole) of 5H-5,6,11,12-tetrahydro dibenz[b,f]azocine (the product of Example 2a), 2.88 g (0.12 mole) of sodium hydride and a small scoop of potassium hydride/mineral oil in 200 ml of dry toluene (argon atmosphere) was stirred and heated to reflux for one hr. The heat was removed and 28.57 g (0.13 mole) of 1-[2-chloro-3-(2-methylpropoxy)propyl]-pyrrolidine was added dropwise with stirring to the hot reaction mixture. The reaction was stirred and heated to reflux for 44 hr then 250 ml of DMF was added dropwise while 250 ml of toluene was distilled off. Refluxing was continued for 2 more hr then the reaction mixture was cooled to RT and 250 ml of ether and 250 ml of water were added. The organic layer was washed with five portions of water, four portions of 1N acetic acid, three portions of 3N sodium hydroxide and dried over anhydrous magnesium sulfate. The dried solution was concentrated in vacuo to give 28.90 g of a crude oily product. The oil was purified by preparative HPLC (Waters Prep 500; silica column; acetone/hexane eluant, 1.5:9 to 1:3) to give 12.5 g of an oil. The oil was chromatographed twice more using acetone/hexane (1:7) to give 8.17 g of still impure oil. The crude oil was finally purified by flash chromatography on silica eluting first with dichloromethane then acetone/dichloromethane (15:85 to 25:75) and evaporated in vacuo to give 6.67 g of pure title product, a golden oil.

Elemental Analysis Calculated for $C_{26}H_{36}N_2O \cdot 0.2\text{-}H_2O$: C, 78.82; H, 9.26; N, 7.07; $H_2O$, 0.91. Found: C, 78.45; H, 8.89; N, 7.03; $H_2O$, 0.6.

EXAMPLE 3

5,6-Dihydro-5-[3-(2,2-dimethylpropoxy)-2-(1-pyrrolidinyl)-propyl]-11H-dibenz[b,e]azepine (E)-2-Butenedioate (Formula (I): $R^1$=CH$_3$; $R^2$=CH$_3$; $R^3$=CH$_3$; W=oxygen; z=—Ch$_2$—; k=1; m=0; n=0; q=1)

(a) α-[(2,2-Dimethylpropoxy)methyl]-1-pyrrolidine ethanol

To a stirred mixture of 92.53 g (1.0 mole) of epichlorohydrin and 88.15 g (1.0 mole) of neopentyl alcohol was added 0.26 g (0.001 mole) of stannic chloride. The reaction temperature rose to about 60° C. then exothermed to about 130° C. in a few seconds. The reaction mixture was stirred until the temperature receded to about 40° C. then 71.12 g (1.0 mole) of pyrrolidine was added. The reaction mixture was stirred and heated to about 95° C. for 1 hr. After cooling the reaction mixture to RT, a mixture of 80 g of 50% sodium hydroxide solution and 80 g of ice was added. The reaction mixture was stirred and heated to 90° C. for 0.5 hr then cooled to RT. The reaction mixture was partitioned between 400 ml of ice water and 400 ml of ether. The organic layer was dried and concentrated in vacuo to give 181 g of oil. The oil was distilled (89°–115° C. at 0.25 mm) to give 136 g of oil that crystallized on standing, 99.1% pure by g.c.

(b) 1-[2-Chloro-3-(2,2-dimethylpropoxy)propyl]pyrrolidine

Dry hydrogen chloride gas was bubbled into an ice-cooled solution of 107.7 g (0.5 mole) of α-[(2,2-dimethylpropoxy)methyl]-1-pyrrolidineethanol (the product of Example 3a) in 110 ml of dry toluene until 20.05 g (0.55 mole) was taken up. This solution was added to a stirred ice-cooled suspension of 109.4 g (0.525 mole) of phosphorous pentachloride in 60ml of dry toluene (argon atmosphere) at a rate to keep the reaction temperature between 10°–15° C. After the addition was complete, the ice bath was removed and the reaction mixture was stirred for 1.5 hr. The reaction mixture was added to a stirred ice-cooled solution of 385 ml (4.5 mole) of 45% potassium hydroxide and 700 ml of ice at a rate to keep the reaction temperature between 25°–35° C. The reaction mixture was stirred for 0.5 hr then extracted with toluene. An immiscible oil formed between the layers. The oil was partitioned between dichloromethane and water. The dichloromethane layer and the toluene layer above were combined, dried and concentrated to dryness to give 84.3 g of oil. The oil was distilled (65°–86° C. at 0.35 mm) to give 76.63 g of oily product.

(c) 5,6-Dihydro-5-[3-(2,2-dimethylpropoxy)-2-(1-pyrrolidinyl)propyl]-11H-dibenz[b,e]azepine (E)-2-Butenedioate To a stirred solution of 15.62 g (0.08 mole) of morphanthridine (prepared by the method described by L. H. Werner et al. in J. Med. Chem., Vol. 8, pp 74–80 (1965)) in 175 ml of dry THF (argon atmosphere) was added 60 ml (0.09 mole) of 1.5M methyl lithium in ether while cooling to −50° C. The cooling bath was removed and the reaction mixture was stirred as is for one hr. The reaction mixture was cooled to −15° C. and 18.70 g (0.08 mole) of 1-[2-chloro-3-(2,2-dimethylpropoxy)propyl]pyrrolidine (the product of Example 3b) was added dropwise. The cooling bath was removed, stirring was continued for one hr, then the reaction mixture was heated to reflux for 20 hr. DMF (150 ml) was added while THF (150 ml) was distilled off. The reaction was then refluxed for 1.5 hr. The reaction mixture was diluted with 300 ml of ether and washed with water. The organic layer was dried over anhydrous magnesium sulfate and evaporated in vacuo to yield 36.04 g of an oil. The crude oil was chromatographed twice on a Waters Prep 500 HPLC (silica column; acetone/hexane eluant (1:8 to 1:4) and acetone/hexane (1:8)) to give 12.92 g of nearly pure free base of the title compound. The oil was converted to the fumarate salt in 2-propanol and crystallized by the addition of hexane. The resulting solid was recrystallized from 2-propanol/hexane to give 10.5 g of the title compound, a light cream-colored solid, mp 148°–150° C.

Elemental Analysis Calculated for C$_{26}$H$_{36}$N$_2$O·C$_4$H$_4$O$_4$: C, 70.84; H, 7.93; N, 5.51. Found: C, 71.14; H, 8.13; N, 5.33.

EXAMPLE 4

10,11-Dihydro-5-[3-(2-methylpropoxy)-2-(1-pyrrolidinyl)-propyl-5H-dibenz[b,f]azepine Hydrochloride (Formula (I): $R^1$=H; $R^2$=CH$_3$; $R^3$=CH$_3$; W=oxygen; Z=—(CH$_2$)$_2$—; A=pyrrolidine; k=0; m=0; n=0; q=1) In a 500 ml three neck round bottom flask (argon atmosphere) was placed 100 ml of dry THF and 15.62 g (0.08 mole) of 10,11-dihydro-5H-dibenz[b,f]azepine (Aldrich). The solution was stirred and cooled to −50° C. while 60 ml (0.084 mole) of 1.4M methyl lithium in ether was added dropwise. When the addition was complete, the cooling bath was removed and the reaction was stirred at ambient temperature for two hr. To the stirred reaction mixture was added a solution of 17.58 g (0.08 mole) of 1-[2-chloro-3-(2-methylpropoxy)propyl]pyrrolidine in 25 ml of dry THF. The reaction mixture was stirred at RT for two hr then heated to reflux for 41 hr. The reaction mixture was cooled to RT and diluted with 200 ml of ether and 100 ml of water. The layers were separated and the organic phase dried over anhydrous magnesium sulfate. The drying agent was removed and the dried solution concentrated in vacuo to give 27.88 g of an oil. The oil was purified on a Waters Prep 500 HPLC (silica column, acetone/hexane eluant (2:98 to 5:95)) to give 12.73 g of an oil. The oil was dissolved in acetone/ether/hexane and extracted with 3N hydrochloric acid. The aqueous layer and an interstitial oil were combined and extracted with dichloromethane. The organic layer was dried over anhydrous magnesium sulfate and concentrated in vacuo to give 16.7 g of an oil that crystallized on standing. The solid was triturated with ether and the insoluble portion was recrystallized twice from toluene/hexane to give 11.42 g of the title compound, a white solid, mp 147°–149° C.

Elemental Analysis Calculated for C$_{25}$N$_{34}$N$_2$O·HCl: C, 72,35; H, 8.50; N, 6.75. Found: C, 72.66; H, 8.54; N, 6.69.

EXAMPLE 5

10,11-Dihydro-10-[3-(2,2-dimethylpropoxy)-2-(1-pyrrolidinyl)propyl]dibenz[b,f][1,4]oxazepine (E)-2-Butenedioate (Formula (I): $R^1=CH_3$; $R^2=CH_3$; $R^3=CH_3$; W=oxygen; Z=oxygen; k=1; m=0; n=0; q=1 )

(a) 10,11-Dihydro dibenz[b,f][1,4]oxazepine

In a one liter three neck flask (argon atmosphere) was placed 50 ml of dry THF and 7.97 g (0.21 mole) of LAH. The suspension was stirred and a warm suspension of 29.57 g (0.14 mole) of 10,11-dihydro dibenz[b,f][1,4]oxazepine-11-one (Aldrich) in 500 ml of THF was added in a slow stream. The reaction mixture was stirred and heated to reflux for 3 hr. The reaction mixture was cooled and cautiously treated with 15 ml of water and 15 ml of saturated sodium sulfate solution. The mixture was stirred and heated to reflux for one hr. The solids were removed by filtration and washed with THF. The filtrate was concentrated to dryness to give 26.90 g of an oil that crystallized on standing. The nearly pure crystalline product was used in the next step without further purification.

(b) 10,11-Dihydro-10-[3-(2,2-dimethylpropoxy)-2-(1-pyrrolidinyl)propyl]dibenz[b,f][1,4]oxazepine (E)-2-Butenedioate To a stirred solution of 9.86 g (0.05 mole) of 10,11-dihydro dibenz[b,f][1,4]oxazepine (the product of Example 5a) in 100 ml of dry toluene (argon atmosphere) was added dropwise 34 ml (0.05 mole) of 1.5 M methyl lithium in ether. The reaction mixture was stirred as is for one hr then 11.69 g (0.05 mole) of 1-[2-chloro-3 (2,2-dimethylpropoxy)propyl]pyrrolidine (the product of Example 3b) was added dropwise. The reaction mixture was stirred and heated to reflux for 3.5 hr. The mixture was cooled to room temperature, diluted with 300 ml of ether and extracted with water. The organic layer was dried over anhydrous magnesium sulfate and concentrated in vacuo to give 23.27 g of an oil. The oil was converted to the fumarate salt in 2-propanol and crystallized by the addition of hexane. The pure title compound was obtained by recrystallization from 2-propanol/hexane, yielding 18.82 g of a light tan solid, mp 142.5°–145.5° C.

Elemental Analysis Calculated for $C_{25}H_{34}N_2O_2 \cdot C_4H_4O_4$: C, 68.21; H, 7.50; N, 5.49. Found: C, 68.40; H, 7.63; N, 5.48.

EXAMPLE 6

5-[3-(2,2 Dimethylpropxy)-2-(1-pyrrolidinyl)propyl]-5H-dibenz[b,f]azepine Hydrochloride (Formula (I): $R^1=CH_3$; $R^2=CH_3$; $R^3=CH_3$; W=oxygen; Z=—CH=CH—; A=pyrrolidine; k=0; m=0; n=0; q=1)

A mixture of 11.60 g (0.06 mole) of iminostilbene (Aldrich), 1.60 g (0.066 mole) of sodium hydride and a small scoop of potassium hydride/mineral oil in 150 ml of dry toluene (argon atmosphere) was stirred and heated to about 100° C. while a solution of 15.43 g (0.066 mole) of 1-[2-chloro-3-(2,2-dimethylpropoxy)-propyl]pyrrolidine (the product of Example 3b) in 25 ml of dry toluene was added dropwise. The reaction mixture was stirred and heated to reflux for 72 hr and then cooled to room temperature, diluted with ether and extracted with water and 3N hydrochloric acid. During the acid extraction an oil formed between the layers which was combined with the aqueous acid layer and the whole was extracted with chloroform. The chloroform layer was dried over anhydrous magnesium sulfate and concentrated in vacuo to give 19.46 g of an oil. The oil was dissolved in chloroform, extracted with 3N sodium hydroxide solution, dried and concentrated in vacuo to give 15.38 g of crude oily free base of the title compound. The oil was purified by chromatography on a Waters Prep 500 HPLC (silica column; acetone/hexane eluant (1:9)) to give 4.28 g of essentially pure free base, an oil. The oil was converted to the hydrochloride salt in ethyl acetate and crystallized by the addition of ether and hexane to give 2.79 g of tan solid. Recrystallization from ethyl acetate/ether yielded 2.25 g of the title compound, a tan solid, mp 167°–168° C.

Elemental Analysis Calculated for $C_{26}H_{34}N_2O \cdot HCl$: C, 73.13; H, 8.26; N, 6.56; Cl, 8.30. Found: C, 72.94; H, 8.30; N, 6.52; Cl, 8.35.

EXAMPLE 7

10-[3-[(1-Methylcyclohexyl)methoxy]-2-(1-pyrrolidinyl)-propyl]-10H-phenoxazine Hydrochloride (1:1)

(Formula (I): $R^1=CH_3$; $R^2-R^3$=cyclohexyl; W=oxygen; Z=oxygen; A=pyrrolidine; k=0; m=0; n=0; q=1)

(a) 1-Methyl-1-cyclohexylmethanol

A three liter three necked round bottom flask was equipped with a thermometer, magnetic stirrer, argon inlet and outlet adapters and a one liter addition funnel containing 922 ml of 1.0 molar $BH_3 \cdot THF$. 1-Methyl cyclohexanecarboxylic acid (119.2 g; 0.84 mole) was added to the reaction vessel and dissolved in 100 ml of THF. The reaction mixture was cooled with an ice bath to 5° C. the $BH_3 \cdot THF$ was added dropwise over 25 min maintaining the temperature between 5°–15° C. After the addition was complete, the ice bath was removed. After about 5 min, the reaction exothermed and foamed violently. A much slower addition rate and constant cooling should help to avoid this exotherm. The reaction was allowed to stir for 2 hr at room temperature under nitrogen, then 150 ml of methanol was added cautiously. When the foaming ceased, the reaction was concentrated in vacuo using low heat and the residue was treated with 100 ml of 5% acetic acid. After stirring for 30 min, the reaction was transferred to a one liter separatory funnel, diluted with water (slurry dissolved) and extracted three times with ether. The combined ether extracts were washed twice with saturated sodium bicarbonate, twice with brine, dried over anhydrous magnesium sulfate, filtered through celite and concentrated in vacuo (low heat) to give 79.09 g of a clear water-white oil. The oil was distilled on a Kugelrohr apparatus at 75°–130° C. (25 mm of Hg). Most distilled at 90° C. to give 72.11 g of 1-methyl-1-cyclohexylmethanol.

(b) alpha-[((1-Methylcyclohexyl)methoxy)methyl]-1-pyrrolidineethanol

A two liter three necked round bottom flask was equipped with a mechanical stirrer, condenser, thermometer, two neck adapter, drying tube and a nitrogen inlet. 1-Methyl-1-cyclohexylmethanol (71.2 g; 0.555 mole) (the compound of Example 7a) was added to the reaction vessel followed by 100 ml of xylene and 43.4 ml (0.555 mole) of epichlorohydrin. The reaction was heated to 50° C. while stirring under nitrogen. 1.45 g (0.0056 mole) of SnCl$_4$ was added. The reaction exothermed suddenly to 140° C. and slowly cooled to 50° C. The reaction was kept at 50° C. in a water bath for 1.5 hr, then cooled to 5°C. with an ice bath. Cold 20% sodium hydroxide (prepared from 40 g of 50% NaOH) was added followed by 47.4 g (0.666 mole) of pyrrolidine. The ice bath was removed, the reaction was heated to reflux for one hr, cooled to RT, diluted with about one liter of water and extracted twice with ether. The combined ether extracts were washed with water, brine, dried over anhydrous potassium carbonate, filtered through dicalite and concentrated in vacuo to give 143.39 g of crude product a light yellow viscous oil. The crude oil was distilled twice to yield 7.6 g (55%) of the title compound, bp 139°-154° C. (0.025 mm).

(c)
1-[2-Chloro-3-(1-methylcyclohexyl)methoxypropyl]-pyrrolidine

A 500 ml three necked round bottom flask was equipped with a mechanical stirrer, addition funnel, thermometer and an argon inlet and outlet. PCl$_5$ (33 g; 0.159 mole) and 8 ml of dry toluene was added to the reaction vessel. 8.5 g (0.151 mole) of alpha-[((1-methyl-cyclohexyl)methoxy)methyl]-1-pyrrolidineethanol (the compound of Example 7b) was added to the addition funnel along with 5 ml of toluene. Hydrogen chloride gas was bubbled into the addition funnel until the solution was acidic. The PCl$_5$ suspension was cooled to 10° C. and the amino alcohol hydrochloride solution was added dropwise, maintaining the temperature between 10°-15° C. After the addition was complete, the ice bath was removed and the mixture stirred at RT for 1.5 hr. A two liter beaker containing 116 ml of 45% potassium hydroxide and 210 g of ice was cooled in an ice bath. The reaction mixture (a clear yellow solution) was transferred to a separatory funnel and added portionwise at a rate to keep the reaction temperature at 25°-35° C. Stirring was continued for 0.5 hr after the addition. The reaction was transferred to a two liter separatory funnel and diluted with water and ether. The water layer was extracted twice with ether and the combined ether extracts were washed twice with water, once with brine, dried over anhydrous potassium carbonate and concentrated in vacuo to give 29.12 g of the title compound.

(d)
10-[3-[(1-Methylcyclohexyl)methoxyl-2-(1-pyrrolidinyl)propyl]-10H-phenoxazine Hydrochloride (1:1)

A 200 ml round bottom flask was equipped with an addition funnel, magnetic stirrer, heating mantle, condenser and argon inlet/outlet. Sodium hydride (1.66 g of a 60% oil suspension; 0.042 mole) was added, washed twice with pentane and then suspended in 35 ml of dry toluene. Potassium hydride (about 30 mg) was added and the mixture heated to reflux while stirring under argon. Phenoxazine (6.34 g; 0.0346 mole; Aldrich) and 9.48 g (0.034 mole) of 1-[2-chloro-3-(1-methylcyclohexyl)methoxypropyl]pyrrolidine (the product of Example 7c) were dissolved in 60 ml of warm dry toluene and added dropwise to the stirred hydride suspension. The mixture was heated to reflux for 2.5 hr and then cooled to room temperature under argon. Water was added cautiously dropwise to destroy excess hydrides and about 50 ml of ether added. After extraction, the aqueous layer was extracted again with ether and the combined ether extracts washed twice with brine, dried over anhydrous potassium carbonate, filtered and evaporated in vacuo to give 13.78 g of a dark brown oil. The oil was dissolved in 75 ml of ethyl acetate and treated with excess ethereal hydrogen chloride to yield a solid. The solid was filtered and washed with ether/ethyl acetate (1:1) then ether to give 13.78 g of an off-white solid. The solid was recrystallized from methylene chloride/ethyl acetate to give 10.49 g of crystalline title compound, a white solid, mp 195°-197° C.

Elemental Analysis Calculated for C$_{27}$H$_{36}$N$_2$O$_2$·HCl: C, 70.95; H, 8.16; N, 6.13. Found: C, 71.05; H, 8.21; N, 6.10.

EXAMPLE 8

5-[3-[(1-Methylcyclohexyl)methoxyl-2-(1-pyrrolidinyl)-propyl]-5H-dibenz [b,f]azepine Hydrochloride (Formula (I): R$^1$=CH$_3$; R$^2$-R$^3$=cyclohexyl; W=oxygen; Z=—CH=CH—; A=pyrrolidine; k=0; m=0; n=0; q=1)

In a 500 ml three neck round bottom flask (argon atmosphere) was placed 100 ml of dry toluene, 1.32 g (0.04 mole) of 80% sodium hydride/mineral oil and a small scoop of potassium hydride/mineral oil. The mixture was stirred and heated to reflux while a warm suspension of 7.73 g (0.04 mole) of imino stilbene (Aldrich) and 10.31 g (0.04 mole) of 1-[2-chloro-3-(1-methyl cyclohexyl)methoxypropyl]pyrrolidine (the Product of Example 7c) in 100 ml of dry toluene was added dropwise over a 20 min period. The reaction mixture was stirred and heated to reflux for six hr. The mixture was cooled to room temperature and 5 ml of methanol was added followed by 100 ml of ether and 200 ml of water. The layers were separated and the organic layer washed with three portions of water, five portions of 3N hydrochloric acid, two portions of 3N sodium hydroxide and one portion of saturated sodium chloride. The organic layer was dried over anhydrous magnesium sulfate and concentrated in vacuo to give 15.94 g of an oil and solid. The oil/solid was mixed with hexane and the insoluble solid removed by filtration. The filtrate was concentrated to dryness in vacuo to give 14.38 g of oil which was purified by flash chromatography on silica gel using acetone/hexane (1:3) as the eluant. The resulting oil (5.07 g) was dissolved in ethyl acetate and treated with ethereal hydrogen chloride to give the hydrochloride salt. The salt was recrystallized from ethyl acetate to give 3.70 g of the title compound, a bright yellow solid, mp 138°-142° C.

Elemental Analysis Calculated for C$_{29}$H$_{38}$N$_2$O·HCl: C, 74.57; H, 8.42; N, 6.00. Found: C, 74.73; H, 8.48; N, 5.96.

EXAMPLE 9

10-[3-(2-Methylpropoxy)-2-(1-pyrrolidinyl)propyl]-10H-phenothiazine (Formula (I): R$^1$=H; R$^2$=CH$_3$; R$^3$=CH$_3$; W=oxygen; Z=sulfur; A=pyrrolidine; k=0; m=0; n=0; q=1)

In a 500 ml three neck flask (argon atmosphere) was placed 200 ml of dry toluene, 19.93 g (0.10 mole) of phenothiazine, 2.64 g (0.11 mole) of sodium hydride and a small scoop of potassium hydride/mineral oil. The reaction mixture was stirred and heated to reflux while 24.17 g (0.11 mole) of 1-[2-chloro-3-(2-methylpropoxy)-propyl]pyrrolidine was added dropwise over a 35 min period. The reaction mixture was stirred and heated to reflux for 46 hr, then cooled to room temperature and treated with 100 ml of water (cautiously at first). The layers were separated and the organic layer was washed with water and with 1N acetic acid. The organic layer was dried over anhydrous magnesium sulfate and concentrated to dryness on a rotary evaporator to give 32.85 g of an oil. A 22.22 g portion of the oil was portioned between ether and 3N hydrochloric acid. The aqueous layer and the interstitial oil were combined, made basic with 3N sodium hydroxide and extracted with dichloromethane. The organic layer was dried over anhydrous magnesium sulfate and concentrated to dryness on a rotary evaporator to give 11.20 g of a two-component oil. The oil was purified on a Waters Prep 500 HPLC (silica column; acetone/hexane eluant, 5:95) to give 3.39 g of a higher $R_f$ component as an oil and 4.06 g of a lower $R_f$ component as an oil. The 4.06 g portion of oil was dissolved in hexane, treated with charcoal, filtered and the solvent removed to vacuo to give 3.92 g of the title compound, a yellow oil.

Elemental Analysis Calculated for $C_{23}H_{30}N_2OS$: C, 72.21; H, 7.90; N, 7.32. Found: C, 72.85; H, 8.18; N, 6.78.

EXAMPLE 10

5-[3-(2-Methyl-2-propenoxy)-2-(1-pyrrolidinyl)]-propyl]5H-dibenz [b,f]azepine Hydrochloride (1:1)

(Formula (I): $C(R^1R^2R^3)=(C=CH_2)CH_3$; W=oxygen; Z=—CH=CH—; A=pyrrolidine; k=0; m=0; n=0; q=1)

In a 1 liter three neck round bottom flask (argon atmosphere) was placed 50 ml of dry toluene, 3.60 g (0.12 mole) of 80% sodium hydride/mineral oil and a small scoop of 35% potassium hydride/mineral oil. The mixture was stirred and heated to reflux and a warm suspension of 19.32 g (0.10 mole) of iminostilbene and 23.95 g (0.11 mole) of 1-[2-chloro-3-(2-methyl-2-propenoxy)propyl]pyrrolidine from Overlook Industries Inc., Bloomsbury, N.J. 08804 in 200 ml of dry toluene was added dropwise over a 45 min period. The reaction mixture was stirred and heated to reflux for 2 hr. The reaction mixture was cooled to RT, diluted with 300 ml of ether and extracted with five portions of water and one portion of saturated sodium chloride solution. The organic layer was dried (anhydrous magnesium sulfate) and concentrated to dryness on a rotary evaporator to give 39.88 g of oil that partially crystallized on standing. The residue was triturated with hexane and the insoluble solid was removed by filtration. The soluble portion was concentrated to dryness on a rotary evaporator to give 37.73 g of oil. A 4.0 g sample of the oil was dissolved in dichloromethane and extracted with two portions of 3N sodium hydroxide solution, two portions of 3N hydrochloric acid and one portion of saturated sodium chloride solution. The organic layer was dried (anhydrous magnesium sulfate) and concentrated to dryness on a rotary evaporator to give 4.32 g of foam. The residue was dissolved in dichloromethane. Ethyl acetate was added and as the dichloromethane was boiled off, crystals formed. Vacuum filtration gave 2.66 g of gray solid. The solid was recrystallized from dichloromethane/ethyl acetate/ether to give 2.24 g of gray solid, mp 122°–126° C.

Elemental Analysis Calculated for $C_{25}H_{30}N_2 \cdot HCl$: C, 73.06; H, 7.60; N, 6.82. Found: C, 72.76; H, 7.72; N, 6.74.

What is claimed is:

1. A propylamine of the following formula (I):

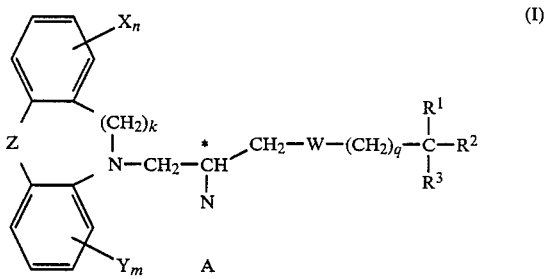

wherein
$R^1$, $R^2$ and $R^3$ are independently hydrogen, lower alkyl or lower alkenyl groups or —$CR^1R^2R^3$ represents a lower alkenyl group, or $R^1$ is a hydrogen, lower alkyl or lower alkenyl group and $R^2$ and $R^3$ are joined to form a cycloalkyl group of 3 to 8 carbons or $R^1$, $R^2$ and $R^3$ are joined to form a polycyclicalkyl group of 7 to 12 carbons;
W is an oxygen or a sulfur atom;
X is independently selected from the group consisting of halo, lower alkyl, lower alkoxy, trifluoromethyl, hydroxy, or, when n is 2 on adjacent carbons, methylenedioxy;
Y is independently selected from the group consisting of halo, lower alkyl, lower alkoxy, trifluoromethyl, hydroxy, or, when m is 2 on adjacent carbons, methylenedioxy;
Z is —$(CH_2)_p$—, —$CR^4=CR^5$— or —$CHR^4$—$CHR^5$—
$R^4$ is hydrogen or lower alkyl;
$R^5$ is hydrogen or lower alkyl;
A represents the atoms necessary to form a pyrrolidine, piperidine or morpholine ring;
k is 0 or 1;
m is 0, 1, 2 or 3;;
n is 0, 1, 2 or 3;
p is 1, 2 or 3;
q is 0 or 1,
and the pharmaceutically acceptable acid addition salts thereof.

2. The propylamine of claim 1, wherein $R^1$, $R^2$ and $R^3$ are independently hydrogen, lower alkyl of 1 to 8 carbons or lower alkenyl of 2 to 8 carbons or —$CR^1R^2R^3$ represents a lower alkenyl group of 2 to 5 carbons, or $R^1$ is hydrogen, lower alkyl of 1 to 8 carbons or lower alkenyl of 2 to 8 carbons and $R^2$ and $R^3$ are joined to form a cycloalkyl group of 3 to 8 carbons or $R^1$, $R^2$ and $R^3$ are joined to form a polycyclicalkyl group of 7 to 12 carbons;
$R^4$ is hydrogen or lower alkyl of 1 to 4 carbons;
$R^5$ is hydrogen or lower alkyl of 1 to 4 carbons;
W is oxygen;
X is independently selected from the group consisting of fluoro, chloro, bromo or iodo, lower alkyl of 1 to 6 carbons; lower alkoxy of 1 to 6 carbons; trifluoromethyl; hydroxy; or, when n is 2 on adjacent carbons, methylenedioxy; and
Y is independently selected from the group consisting of fluoro, chloro, bromo or iodo; lower alkyl of 1 to 6 carbons; lower alkoxy of 1 to 6 carbons; trifluoromethyl; hydroxy; or, when m is 2 on adjacent carbons, methylenedioxy.

3. The propylamine of claim 1, wherein
$R^1$ is hydrogen or lower alkyl or 1 to 8 carbons and $R^2$ and $R^3$ are loweralkyl of 1 to 8 carbons or $R^1$ is lower alkyl of 1 to 8 carbons and $R^2$ and $R^3$ are joined to form a cyclohexyl group, or —$CR^1R^2R^3$ represents a lower alkenyl group of 2 to 4 carbons;
$R^4$ is hydrogen;
$R^5$ is hydrogen;
A represents the atoms necessary to form a pyrrolidine ring;
m is 0;
n is 0;
p is 1 or 2; and,
q is 1.

4. The propylamine of claim 2, wherein $R^1$, $R^2$ and $R^3$ are each methyl.

5. The propylamine of claim 2, wherein $R^1$ is methyl and $R^2$ and $R^3$ are joined to form a cyclohexyl group.

6. The propylamine of claim 2, wherein —$CR^1R^2R^3$ represents a lower alkenyl group of 2 to 4 carbons.

7. The propylamine of claim 2, wherein $R^1$ is hydrogen and $R^2$ and $R^3$ are each methyl.

8. The propylamine of claim 1, wherein Z is —$(CH_2)_p$— or —CH=CH—.

9. The propylamine of claim 1, wherein q is 1.

10. The propylamine of claim 1, wherein A represents the atoms necessary to form a pyrrolidine ring.

11. The propylamine of claim 1, wherein W is oxygen.

12. The propylamine of claim 1, wherein said pharmaceutically acceptable acid addition salt is one formed with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, 2-acetoxybenzoic or a salt made with saccharin.

13. The propylamine of claim 1, wherein said propylamine is selected from the group consisting of:
5,6-dihydro-5-[3-(2-methylpropoxy)-2-(1-pyrrolidinyl)propyl]-11H-dibenz[b,e]azepine;
5,6,11,12-tetrahydro-5-[3-(2-methylpropoxy)-2-(1-pyrrolidinyl)propyl]dibenz[b,f]azocine;
5,6-dihydro-5-[3-(2,2-dimethylpropoxy)-2-(1-pyrrolidinyl)propyl]-11H-dibenz[b,e]azepine;
5-[3-(2,2-dimethylpropoxy)-2-(1-pyrrolidinyl)]propyl]-5H-dibenz[b,f]azepine;
5-[3-[(1-methyl cyclohexyl)methoxy]-2-(1-pyrrolidinyl)propyl]-5H-dibenz[b,f]azepine; and
5-[3-(2-methyl-2-propenoxy)-2-(1-pyrrolidinyl)propyl]-5H-dibenz[b,f]azepine
or a pharmaceutically acceptable acid addition salt thereof.

14. The propylamine of claim 13, wherein said propylamine is 5,6-dihydro-5-[3-(2-methylpropoxy)-2-(1-pyrrolidinyl)propyl]-11H-dibenz[b,e]azepine or a pharmaceutically acceptable acid addition salt thereof.

15. The propylamine of claim 13, wherein said propylamine is 5-[3-(2,2-dimethylpropoxy)-2-(1-pyrrolidinyl)propyl]5H-dibenz[b,f]azepine or a pharmaceutically acceptable acid addition salt thereof.

16. A pharmaceutical composition which comprises a propylamine of claim 1 in association with a pharmaceutically acceptable diluent or carrier.

17. A method for the treatment of hypertension in a mammal which comprises administering to the mammal the composition of claim 16.

18. The method of claim 17, wherein said mammal is a human.

19. A method for the treatment of angina in a mammal which comprises administering to the mammal the composition of claim 16.

20. The method of claim 19, wherein said mammal is a human.

* * * * *